US00PP21951P2

(12) United States Plant Patent
Akai

(10) Patent No.: US PP21,951 P2
(45) Date of Patent: May 31, 2011

(54) ***PETUNIA* PLANT NAMED 'AK101'**

(50) Latin Name: *Petunia×hybrida*
Varietal Denomination: AK101

(75) Inventor: Nobutaka Akai, Miyazaki (JP)

(73) Assignee: Suntory Flowers Ltd., Tokyo (JP)

( * ) Notice: Subject to any disclaimer, the term of this patent is extended or adjusted under 35 U.S.C. 154(b) by 0 days.

(21) Appl. No.: 12/658,729

(22) Filed: Feb. 12, 2010

(51) Int. Cl.
*A01H 5/00* (2006.01)

(52) U.S. Cl. ..... Plt./356

(58) Field of Classification Search ..... Plt./356
See application file for complete search history.

*Primary Examiner* — Kent L Bell
(74) *Attorney, Agent, or Firm* — C. A. Whealy

(57) ABSTRACT

A new and distinct cultivar of *Petunia* plant named 'AK101', characterized by its compact and trailing plant habit; vigorous growth habit; freely branching and flowering plant habit; long flowering period; small double red purple-colored flowers; and good garden performance.

1 Drawing Sheet

Botanical designation: *Petunia×hybrida*.
Cultivar denomination: 'AK101'.

BACKGROUND OF THE INVENTION

The present invention relates to a new and distinct cultivar of *Petunia* plant, botanically known as *Petunia×hybrida* and hereinafter referred to by the name 'AK101'.

The new *Petunia* plant is a product of a planned breeding program conducted by the Inventor in Miyazaki-shi, Miyazaki, Japan. The objective of the breeding program is to create new compact *Petunia* plants with attractive double flowers.

The new *Petunia* plant originated from a cross-pollination made by the Inventor in June, 2006 in Miyazaki-shi, Miyazaki, Japan of two unnamed proprietary selections of *Petunia×hybrida*. The new *Petunia* plant was discovered and selected by the Inventor as a single flowering plant within the progeny of the stated cross-pollination in a controlled environment in Miyazaki-shi, Miyazaki, Japan in March, 2007.

Asexual reproduction of the new *Petunia* plant by terminal cuttings in a controlled environment in Miyazaki-shi, Miyazaki, Japan since April, 2007, has shown that the unique features of this new *Petunia* plant are stable and reproduced true to type in successive generations.

SUMMARY OF THE INVENTION

Plants of the new *Petunia* have not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'AK101'. These characteristics in combination distinguish 'AK101' as a new and distinct cultivar of *Petunia:*

1. Compact and trailing plant habit.
2. Vigorous growth habit.
3. Freely branching and flowering plant habit.
4. Long flowering period.
5. Small double red purple-colored flowers.
6. Good garden performance.

Plants of the new *Petunia* can be compared to plants of the female parent selection. Plants of the new *Petunia* differ primarily from plants of the female parent selection in the following characteristics:

1. Plants of the new *Petunia* are more trailing than and not as upright as plants of the female parent selection.
2. Plants of the new *Petunia* have shorter internodes than plants of the female parent selection.
3. Flowers of plants of the new *Petunia* have more petals than flowers of plants of the female parent selection.

Plants of the new *Petunia* can be compared to plants of the male parent selection. Plants of the new *Petunia* differ primarily from plants of the male parent selection in the following characteristics:

1. Plants of the new *Petunia* have shorter internodes than plants of the male parent selection.
2. Plants of the new *Petunia* and the male parent selection differ in flower type as plants of the male parent selection have single flowers.
3. Plants of the new *Petunia* and the male parent selection differ in flower color as plants of the male parent selection have purple-colored flowers.

Plants of the new *Petunia* can also be compared to plants of the *Petunia* 'Bluette Rose Vivid Pink', not patented. In side-by-side comparisons conducted in Miyazaki-shi, Miyazaki, Japan, plants of the new *Petunia* and 'Bluette Rose Vivid Pink' differed primarily in the following characteristics:

1. Plants of the new *Petunia* were more compact than plants of 'Bluette Rose Vivid Pink'.
2. Plants of the new *Petunia* had shorter lateral branches than plants of 'Bluette Rose Vivid Pink'.
3. Plants of the new *Petunia* were more freely flowering than plants of 'Bluette Rose Vivid Pink'.
4. Flowers of plants of the new *Petunia* had more petals than flowers of plants of 'Bluette Rose Vivid Pink'.

BRIEF DESCRIPTION OF THE PHOTOGRAPHS

The accompanying colored photographs illustrate the overall appearance of the new *Petunia* plant, showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet comprises a side perspective view of a typical flowering plant of 'AK101' grown in a container.

The photograph at the bottom of the sheet is a close-up view of typical flowers of 'AK101'.

DETAILED BOTANICAL DESCRIPTION

The aforementioned photographs and following observations, measurements and values describe plants grown in 15-cm containers in Higashiomi, Shiga, Japan, under commercial practice during the late spring and early summer in an outdoor nursery with day temperatures averaging 23° C. and night temperatures averaging 13° C. Plants were four months old when the photographs and description were taken. In the following description, color references are made to The Royal Horticultural Society Colour Chart, 2001 Edition, except where general terms of ordinary dictionary significance are used.

Botanical classification: *Petunia×hybrida* 'AK101'.

Parentage:

*Female, or seed, parent.*—Unnamed proprietary selection of *Petunia×hybrida*, not patented.

*Male, or pollen, parent.*—Unnamed proprietary selection of *Petunia×hybrida*, not patented.

Propagation:

*Type.*—By terminal cuttings.

*Time to initiate roots, summer.*—About eight days at temperatures of 30° C. to 35° C.

*Time to initiate roots, winter.*—About twelve days at temperatures of 20° C. to 22° C.

*Time to produce a rooted young plant, summer.*—About 15 days at temperatures of 30° C. to 35° C.

*Time to produce a rooted young plant, winter.*—About 20 days at temperatures of 20° C. to 22° C.

*Root description.*—Fibrous; white in color.

*Rooting habit.*—Freely branching.

Plant description:

*Plant and growth habit.*—Compact and trailing plant habit; freely branching habit with numerous lateral branches developing per plant; pinching enhances lateral branch development; vigorous growth habit.

*Plant height.*—About 13 cm.

*Plant diameter.*—About 42.8 cm.

Lateral branch description:

*Length.*—About 23.2 cm.

*Diameter.*—About 2.4 mm.

*Internode length.*—About 1.5 cm.

*Strength.*—Strong, flexible.

*Aspect.*—Decumbent.

*Texture.*—Pubescent.

*Color.*—Close to 143C.

Foliage description:

*Arrangement.*—Alternate, simple.

*Length.*—About 4.9 cm.

*Width.*—About 2 cm.

*Shape.*—Ovate.

*Apex.*—Acute.

*Base.*—Cuneate to obtuse.

*Margin.*—Entire.

*Texture, upper and lower surfaces.*—Pubescent.

*Venation pattern.*—Pinnate; reticulate.

*Color.*—Developing and fully expanded leaves, upper surface: Close to 137C; venation, close to 144B. Developing and fully expanded leaves, lower surface: Close to 146B; venation, close to 144B.

*Petioles.*—Length: About 7.5 mm. Diameter: About 2.3 mm. Texture, upper and lower surfaces: Pubescent. Color, upper and lower surfaces: Close to 144B.

Flower description:

*Flower arrangement and habit.*—Double flowers arising from leaf axils; freely flowering habit with usually about 77 open flowers per plant; flowers face upright to outwardly.

*Fragrance.*—None detected.

*Natural flowering season.*—Early flowering habit, plants of the new *Petunia* initiate and develop flowers about three to four weeks after planting; long flowering period, flowering commences naturally during the spring and plants flower continuously throughout the summer until late autumn in Japan.

*Flower longevity.*—Individual flowers last about seven to ten days on the plant; flowers persistent.

*Flower diameter.*—About 3.9 cm.

*Flower length (depth).*—About 2.6 cm.

*Tube diameter, base.*—About 4.8 mm.

*Tube length.*—About 1.6 cm.

*Flower bud.*—Shape: Cylindrical. Length: About 2.2 cm. Diameter: About 7.6 mm. Color: Close to 76D; venation, close to N77C.

*Corolla.*—Arrangement: About 50 petals arranged in four to five whorls and fused at the base. Petal length from throat: About 0.4 cm to 1.5 cm. Petal width: About 0.2 cm to 2.2 cm. Petal shape: Spatulate. Petal apex: Acute to cuspidate. Petal margin: Entire. Petal texture, upper and lower surfaces: Smooth, glabrous. Throat texture: Smooth, glabrous. Tube texture: Pubescent. Color: Petal, when opening and fully opened, upper surface: Close to N74A; venation, close to N74A. Petal, when opening and fully opened, lower surface: Close to 75C; venation, close to N77C or 148A. Throat: Close to 76D; venation, close to N77C. Tube: Close to 76D; venation, close to N77C.

*Calyx.*—Arrangement: One star-shaped calyx tube with five sepals fused at the base per flower. Sepal length: About 1.1 cm. Sepal width: About 1.2 mm. Sepal shape: Lanceolate. Sepal apex: Acute. Sepal margin: Entire. Sepal texture, upper and lower surfaces: Pubescent. Color, immature and mature, upper surface: Close to 137A. Color, immature and mature, lower surface: Close to 137B.

*Peduncles.*—Length: About 3 cm. Diameter: About 1.2 mm. Strength: Strong. Aspect: Upright to outwardly. Texture: Pubescent. Color: Close to 143C with reddish tinting.

*Reproductive organs.*—Stamens: Quantity/arrangement: None to five per flower. Anther shape: Ellipsoidal. Anther size: About 1 mm by 2.1 mm. Anther color: Close to 11D. Pollen amount: Scarce. Pollen color: Close to 11D. Pistils: Quantity: One per flower. Pistil length: About 1 cm. Style color: Close to 144D. Stigma shape: Transversely ellipsoidal. Stigma color: Close to 144D. Ovary color: Close to 144A.

*Seeds/fruits.*—Seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen/pest resistance: Plants of the new *Petunia* have not been observed to be resistant to pathogens and pests common to *Petunia* plants.

It is claimed:

1. A new and distinct *Petunia* plant named 'AK101' as illustrated and described.

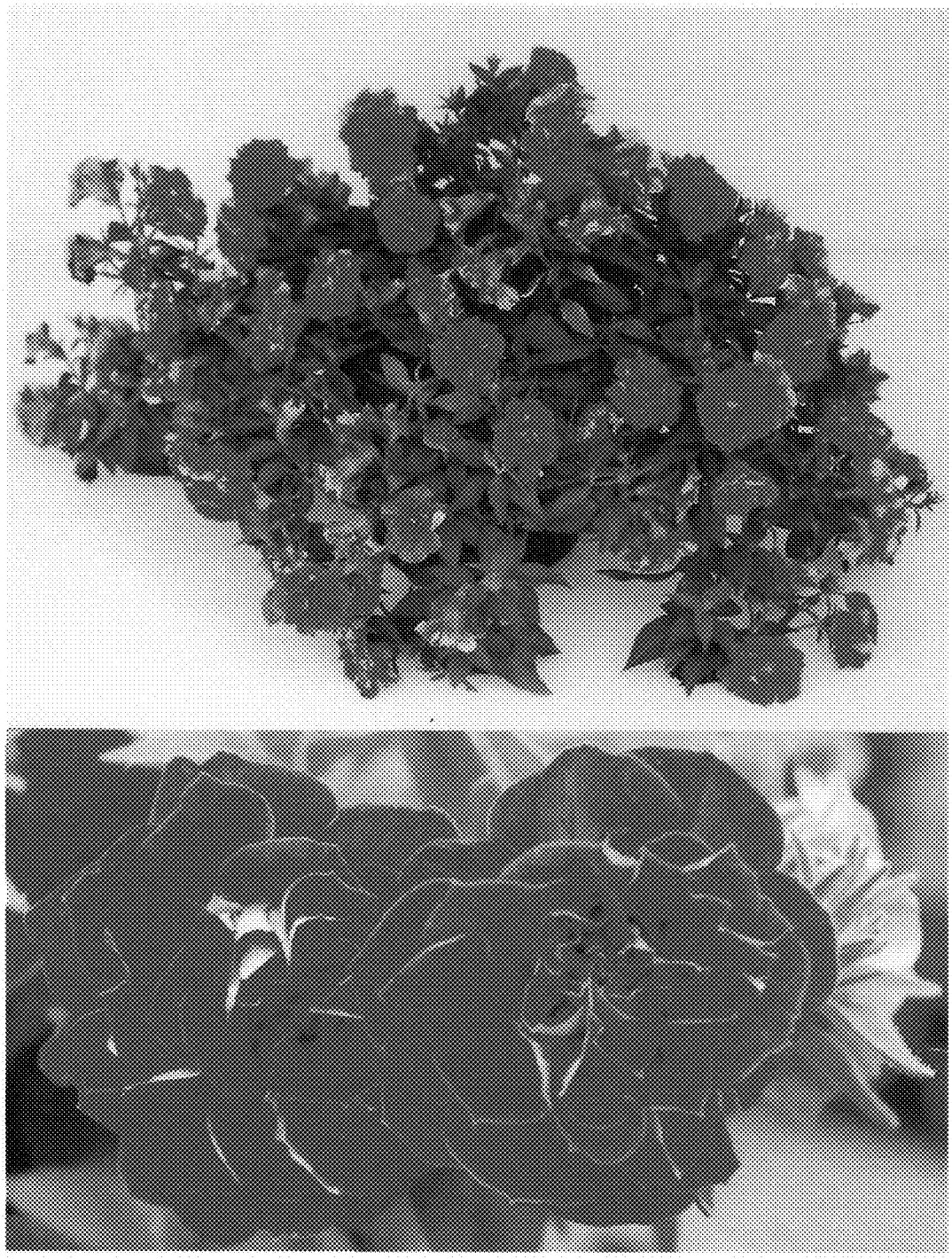

* * * * *